United States Patent
Herklotz et al.

(10) Patent No.: US 9,793,580 B2
(45) Date of Patent: Oct. 17, 2017

(54) BATTERY CARRIER FOR IN SITU ANALYSIS

(71) Applicants: Leibniz-Institut für Festkörper- und Werkstoffforschung Dresden e.V., Dresden (DE); Karlsruher Institut für Technologie, Karlsruhe (DE)

(72) Inventors: Markus Herklotz, Dresden (DE); Jonas Weiss, Dresden (DE); Lars Giebeler, Dresden (DE); Michael Knapp, Karlsruhe (DE)

(73) Assignees: Leibniz-Institut für Festkörper- und Werkstoffforschung Dresden e.V., Dresden (DE); Karlsruher Institut für Technologie, Karlsruhe (DE)

( * ) Notice: Subject to any disclaimer, the term of this patent is extended or adjusted under 35 U.S.C. 154(b) by 0 days.

(21) Appl. No.: 15/318,684

(22) PCT Filed: Jun. 17, 2015

(86) PCT No.: PCT/EP2015/063638
§ 371 (c)(1),
(2) Date: Jan. 10, 2017

(87) PCT Pub. No.: WO2015/193393
PCT Pub. Date: Dec. 23, 2015

(65) Prior Publication Data
US 2017/0141443 A1   May 18, 2017

(30) Foreign Application Priority Data
Jun. 20, 2014   (DE) .................. 10 2014 211 901

(51) Int. Cl.
*G01N 23/00*   (2006.01)
*G01N 23/20*   (2006.01)
(Continued)

(52) U.S. Cl.
CPC ........ *H01M 10/4285* (2013.01); *G01N 23/02* (2013.01); *H01M 10/482* (2013.01)

(58) Field of Classification Search
USPC .......... 250/269.1, 269.2, 269.3, 269.4, 269.5, 250/269.6, 269.7, 306, 307, 363.01,
(Continued)

(56) References Cited

U.S. PATENT DOCUMENTS 7,022,290 B2 * 4/2006 Gural .................. G01N 23/20
204/193
9,022,652 B2 * 5/2015 Chupas ............ G01N 23/20025
378/208
(Continued)

FOREIGN PATENT DOCUMENTS

EP     2495748 A1   9/2012
JP    H1054809 A   2/1998
(Continued)

OTHER PUBLICATIONS

Markus Herklotz et al: "Advances in in situ powder diffraction of battery materials: a case study of the new beamline P02.1 at DESY, Hamburg", Journal of Applied Crystallography, vol. 133, No. 4, Aug. 2013, pp. 4404-1127, XP055212001, ISSN: 0021-8898, DOI: 10.1107/S0021889813013551, mentioned in the application; Chapter 2.2; Figures 2-4.

*Primary Examiner* — Bernard Souw
(74) *Attorney, Agent, or Firm* — Michael Soderman (57) ABSTRACT

The subject of the present invention is a device for the in situ analysis of batteries by means of X-ray, synchrotron or another radiation. The device has a sample support, which is realized as a sample wheel rotatably mounted about the center axis. A plurality of sample holders, the center points of which are placed on a common circular line about the center point of the sample support, are arranged on the sample support, wherein each sample holder can be repeat-
(Continued)

edly opened and closed individually by an arrestable cover. Each sample holder has in its interior a cavity which receives the battery, which is to be examined, in a manner ideal in shape with regard to circumference, wherein the cover and the cavity have an opening for the passage of the beam. A spring, engaging in the edge region of the battery, presses the battery against the cover, wherein the spring and the edge region of the cover are embodied so as to be electrically conducting but insulated with respect to one another. There are directed from each sample holder an electrically conductive connection from the edge region of the cover, and an electrically conductive connection from the spring onto the face of the sample support facing away from the cover and into the vicinity of its center point. There, the lines of all sample holders are combined to form a line bundle or a plug connector.

5 Claims, 4 Drawing Sheets

(51) Int. Cl.
*H01M 10/48* (2006.01)
*B01L 9/00* (2006.01)
*H01M 10/42* (2006.01)
*G01N 23/02* (2006.01)

(58) Field of Classification Search
USPC ..... 250/370.09, 526; 378/44–47, 53, 54, 64, 378/71, 73, 75, 81–84, 86, 88–90, 210; 429/48, 50, 51, 57, 96, 99, 100, 121, 122; 204/193, 194, 400
See application file for complete search history.

(56) References Cited

U.S. PATENT DOCUMENTS

2014/0093052 A1* 4/2014 Chupas ............ G01N 23/20025
378/208
2016/0036011 A1* 2/2016 Jung ..................... H01M 10/48
429/174

FOREIGN PATENT DOCUMENTS

JP 2012159311 A 8/2012
WO 9622523 A1 7/1996

* cited by examiner

BATTERY CARRIER FOR IN SITU ANALYSIS

CROSS REFERENCE TO RELATED APPLICATIONS

This application is the U.S. national stage of International Application No. PCT/EP2015/063638, filed on Jun. 17, 2015. The international application claims the priority of DE 102014211901.4 filed on Jun. 6, 2014; all applications are incorporated by reference herein in their entirety.

BACKGROUND

The subject of the present invention is a device which permits batteries, in particular battery button cells, to be introduced into an X-ray beam, synchrotron beam or other probe beam, in order to carry out diffractometric or spectroscopic examination on these batteries during charging or respectively discharging.

Within the development of high-performance batteries, in particular of accumulators, it is of particularly great interest to examine the structural chemical processes which occur during the charging and discharging of the battery system. Such examinations are designated as in situ examinations. In this context, in situ means in particular: the quantitative examination of the crystalline structure, the electrode morphology or the surface chemistry of all components which are involved, whilst the battery is continuously charged and discharged (i.e. without interruption of the current supply).

Examinations by means of X-ray or respectively synchrotron radiation are particularly beneficial and widely-used, because the wavelength thereof lies in the scale range of the atomic structure. This permits a quantitative examination of structural chemical phenomena and a detailed description, for example of phase fractions, lattice parameters or atom positions as a function of the charging status of the battery material. Synchrotron radiation offers extreme temporal and instrumental resolutions and is therefore used most frequently. The housings of the batteries which are to be examined generally have openings for beam entry or respectively beam exit, for the examination. These openings can also be covered by materials which only interact slightly with the radiation which is used.

Radiographic and reflection diffractometry come into use here in particular as methods. The so-called in situ PDF (pair distribution function) methods or fluorescence analysis, in particular absorption spectroscopy are also increasingly carried out.

Whereas in radiographic diffractometry and absorption spectroscopy the diffraction- or respectively absorption pattern, occurring behind the object which is to be examined, is analysed, reflection diffractometry is a method in which both the radiation source and also the detector are arranged above the same surface. The beam diameters of the X-ray or synchrotron radiation are generally less than 3 mm and are mostly even below this (approximately 1 mm).

The radiation time, therefore the time which is available for the diffractometric measurements, is generally small and, in particular in the case of the use of synchrotron radiation, is also particularly expensive. The time available is therefore to be utilized effectively. It is therefore aimed to use as little time as possible for the placing and adjusting of the sample (battery) in the path of rays and to measure as many samples as possible simultaneously (i.e. sequentially). For this purpose, special sample mountings have been developed.

U.S. Pat. No. 5,127,039 describes a sample holder for X-ray diffractometry. A particular characteristic of this development is the adjustability in every spatial direction. The device is also to have a sample holder. The latter is configured rotatably, so that it can rotate during the irradiation. However, provision is not made to insert several samples. The rotational movement refers here only to an individual sample, even if mention is made of a "sample disc" (column 3, II. 1-8). The rotation axis of the sample holder is perpendicular here to the beam axis and intersects the latter. A refitting for measuring the next sample is still time-consuming here, however.

The subject of US 2014/0106216 A1 is a method for subjecting layers, from which a lithium-ion battery is constructed, to a local heat treatment during manufacture. During the manufacturing process, sputtering processes take place, for which the use of a sample holder carousel is proposed. A direct transferability to diffractometric examination does not exist.

US 2014/0093052 A1 proposes a test chamber for X-ray or neutron spectroscopy on batteries and fuel cells. The subjects of the examination do not bring their own housings here, but rather are assembled in the sample chambers of the test chamber. The test chamber is embodied as a two-part housing with an upper part and a lower part. The contacting of the cells takes place via feedthroughs through which the contact lines lead to the battery wall or respectively to the cover of the battery. A disadvantage in this construction is that the contacting of the battery takes place via lines which can not guarantee a reliable making of contact. In particular, the test chamber is therefore only suitable for one single battery size.

U.S. Pat. No. 7,022,290 B2 describes a hermetically sealed examination chamber for batteries. The examination chamber consists of a base body with an insertion opening for the battery and a cover which has an opening for the beam entry. This construction is suitable exclusively for back radiation examinations, because there is no possibility for detecting a beam passing through the battery, because there is no suitable outlet opening.

In WO 96/22523 a device is proposed for the examination of batteries by means of X-radiation. The device consists of an upper part and a lower part, which are electrically insulated from one another. The contacting of the battery takes place via connections on this upper or respectively lower part, whilst the battery is clamped between these parts. The underside of the battery is contacted through a copper block, whilst the upper part is exposed to the radiation via a window. This device is likewise not suitable for radiographic examinations, because the copper block would falsify the measurement results.

In JP 2012-159311 A a device is described which is intended to receive the individual layers of a battery and to make them accessible for examination. Here, the layers of the battery are clamped between two counter-pieces, which have windows for beam entry or respectively exit. This device concerns a solution for handling an individual cell. The positioning in the beam takes place via a special holder for receiving the device. A quick changeover of samples and a reliable voltage supply are thus not guaranteed.

The subject of JP 10-054809 A is a device consisting of an upper part and a lower part, which are electrically insulated with respect to one another. Clamped between these parts is the layer stack of a battery with electrolyte. The contacting takes place via the upper or respectively lower part. The two parts have windows for passage of the beam. The device is not suitable to receive prefabricated battery bodies and to deliver these for a quick measurement. Rather, the device itself is to be regarded as a battery housing for experimental layerings and electrolytes of batteries.

The company Anton Paar (http://www.anton-paar.com/?eID=documentsDownload&document=2065&L=8, webpage status: 18 Jun. 2014) proposes a sample support which has a sample wheel. This is to be situated in a microclimate chamber and the possibility exists to move one of eight samples into an X-ray beam. A radiography of the sample is provided. The sample wheel is aligned substantially horizontally. The sample supports are not able to be closed, so that a change in the position of the sample wheel is not readily possible. Moreover, no individual deliveries of media or of electrical energy are provided to the individual samples. In situ battery examinations are therefore not able to be carried out.

In the article "Advances in in situ powder diffraction of battery materials: a case study of the new beam line P02.1 at DESY, Hamburg", M. Herklotz et al. Journal of Applied Crystallography, (2013). 46. P. 1117-1127 a sample support is shown, which has four battery holders which are arranged around the centre point of the circular sample support. The sample support is also embodied so as to be rotatable about this centre point. Each of the battery holders can be electrically connected, so that in situ measurements are possible. A problem is that the current supply takes place via several cables (2 per battery), which lead in an undefined manner away from the side of the sample support facing the primary beam. It can happen here that during the measuring process or on a rotation of the sample support, cables arrive into the path of rays and lead to a falsification of the measurement results. Furthermore, through the fixing of the sample cover by means of screws, the changeover of samples is laborious, time-consuming and susceptible to error.

SUMMARY

The subject of the present invention is a device for the in situ analysis of batteries by means of X-ray, synchrotron or another radiation. The device has a sample support, which is realized as a sample wheel rotatably mounted about the centre axis. A plurality of sample holders, the centre points of which are placed on a common circular line about the centre point of the sample support, are arranged on the sample support, wherein each sample holder can be repeatedly opened and closed individually by an arrestable cover. Each sample holder has in its interior a cavity which receives the battery, which is to be examined, in a manner ideal in shape with regard to circumference, wherein the cover and the cavity have an opening for the passage of the beam. A spring, engaging in the edge region of the battery, presses the battery against the cover, wherein the spring and the edge region of the cover are embodied so as to be electrically conducting but insulated with respect to one another. There are directed from each sample holder an electrically conductive connection from the edge region of the cover, and an electrically conductive connection from the spring onto the face of the sample support facing away from the cover and into the vicinity of its centre point. There, the lines of all sample holders are combined to form a line bundle or a plug connector.

DETAILED DESCRIPTION

The problem is therefore posed to propose a device as sample support, which is suitable both for radiographic and also for reflection measurements by means of X-rays or synchrotron rays, in particular enables in situ measurements and enables an interference-free supply of media, in reliable manner with regard to handling, to the batteries which are to be examined.

According to the invention, the problem is solved by means of a sample support according to claim 1. Advantageous embodiments are disclosed in the subclaims which refer back thereto.

The sample support according to the invention is embodied as a battery support for the in situ analysis of batteries by means of radiographic or respectively synchrotron diffractometry. It has a sample wheel, mounted rotatably about its centre point. The sample wheel is preferably mounted on its outer edge, particularly via ball bearings.

An alternative embodiment provides for the use of an axis engaging in the centre point of the sample wheel, which axis is mounted accordingly. A plurality of sample holders are arranged around the centre point of the sample wheel, preferably on a circular ring and preferably equidistant to one another, wherein each sample holder can be repeatedly opened and closed individually by an arrestable cover. The sample holder has in its interior a cavity (depression with cover), which receives the battery which is to be examined in a manner ideal in shape with regard to circumference. The cover and depression have a non-closed or covered opening for the passage of rays and a spring engaging in the edge region of the underside of the battery. The spring presses the battery against the cover, which thus contacts electrically the edge region of the upper side of the battery. The spring and at least the edge region of the cover are electrically conducting, but are insulated with respect to one another. In a manner essential to the invention, there is directed an electrically conductive connection from each sample support from the edge region of the cover and an electrically conductive connection from the spring into the vicinity of the centre point of the sample wheel (centre axis). The cover and spring respectively contact here another of the two poles (electrochemically positive and negative electrode) of the battery which is to be examined. The lines of all the sample supports are advantageously combined to form a line bundle in the vicinity of the centre point.

The sample support is preferably embodied as a wheel-like construction. It has here a circular base surface with a centre axis. The sample support is rotatable about this centre axis. A plurality of sample holders are arranged from the centre axis and at an identical distance of their centre points to the latter. The sample holders are preferably arranged at the same distance from one another on the circular ring, which they form owing to their identical distance from the centre axis. With corresponding control of the movement of the sample wheel, however, varying distances between the sampleholders are also possible. Preferably, the sample holders have identical diameters. Further preferably, however, sample holders of differing diameters are also possible. However, it is essential here that the geometric centre points of the sample holders are all arranged on a common circular line around the centre point of the sample support (the specifications refer to the front face of the sample support). Preferably two, three, four, six or eight sample holders are arranged on the sample support. Basically, any expedient number of sample holders is possible. This is limited by the dimensions which are to be adhered to (dependent on the X-ray or synchrotron device) and the measuring tasks.

The sample support is preferably made from plastic, fibre-reinforced plastic or other non-conducting rigid materials. The face facing the primary beam in the case of transmission (therefore the face which is penetrated first by the beam) is designated in the following as the rear face of the sample support, and the face facing away from the beam (therefore in the diffraction region) is designated as the front face.

In a first preferred embodiment, the centre axis is aligned parallel to the axis of the X-ray beam (beam axis). This embodiment is particularly suitable for radiographic measurements (transmission diffractometry).

In a further preferred embodiment, the centre axis stands at an acute angle to the beam axis such that the front face of the sample support, therefore the face on which the covers (see further below) close off the sample holders, faces the incident beam. This embodiment is used in particular in X-ray reflection diffractometry or X-ray fluorescence analysis.

The sample support is preferably provided with a drive which implements the positioning respectively of a sample holder into the path of rays by rotation of the sample support about the centre axis. The drive is preferably an electric stepping motor. In a particularly simple embodiment, the rotation takes place manually in beam pauses.

The sample holders are preferably embodied as depressions in the sample support. They have a shape which is adapted to the battery which is to be examined. The shape is preferably circular, corresponding to the majority of the batteries. The depression is closed by a (preferably circular) cover, which is detachable and able to be arrested in the closure position. The depression preferably narrows beneath its upper edge slightly, so that a shoulder results, on which the cover can rest and where it can be held in its position by projections or screws. In a preferred embodiment, this concerns a simple interlocking of the cover with projections which are arranged on the edge of the depression. The cover has corresponding recesses, so that it can be guided past the projections into the depression and can be arrested behind the projections by a twisting. The projections can also be formed by the heads of screws which are arranged around the depression. Furthermore, it is possible to dispense with the projections and the recesses and to fix the cover in its position entirely by screw heads. However, this does not allow the cover to be opened so quickly as would be the case with an interlocking.

The flat construction of the holder and of the cover advantageously permit a maximum diffraction angle of at least 70° (in the example of transmission with primary beam directing parallel to the rotation axis, specification in 2□□. This increases the range of application in transmission- and reflection arrangement. For example, so-called PDF (pair distribution function) methods can be carried out, which provide detailed knowledge concerning the atomic short-range order, but require a high diffraction angle.

The cover has a preferably central opening for beam entry. In a preferred embodiment, the opening is covered or respectively filled by a material (for example Kapton) slightly influencing the X-ray beam. The cover is preferably made from conductive material or is coated with such a material. In this way, an electrically conductive connection is produced to the upper side of the battery (diffraction region).

A spring which presses the battery, which is to be examined, in the direction of the cover is arranged in the depression. This is preferably a helical spring which engages on the battery at or in the vicinity of the outer edge. In this way, the beam can pass the spring in its interior during continuity measurements without a falsifying influence being exerted by the spring material on the measurement result. The helical spring is preferably made from conductive material, is coated with such a material or is drawn through thereby, so that an electrically conductive connection is achieved from the base of the battery to the base of the depression of the sample holder or the contact surface of a conductor board.

In a preferred embodiment, the spring rests on the base of the depression of the sample holder. The base preferably also has an opening which serves for beam entry. This opening can also be closed or filled by suitable material.

The internal diameter of the spring and the openings in the base and in the cover of the depression are selected so that they exceed the beam diameter, in order to cause no or respectively a minimized interaction with the beam.

Through the spring, it is advantageously possible to insert into the sample holders batteries with different overall heights and with the same external diameters. For example, a changeover can be made without difficulty between cells of the structural forms CR2032, CR2025 or CR2016.

Smaller diameters than the 2 cm typical for the named cells, are also possible. A preferred embodiment has an adapter for this, which is placed as a ring around a battery with a smaller diameter than the depression of the sample holder and thus enables a measuring of batteries of smaller diameters. Attention is to be paid here to the diameter of the spiral spring. Even smaller battery diameters then require a washer, which can reliably prevent a slipping of the battery into the spiral spring.

Through the electrically conductive configuration of the cover, the upper side of the battery is contacted. Starting form the cover, a further conductive connection is produced. This preferably leads as a cable to the front face and from there to the rear face of the sample support. In embodiments in which the cover is held by screw heads, at least one of the screws can also consist of metal and can extend up to the rear face of the sample support. In embodiments which have projections at the edges of the depressions, at least one projection is electrically conductive and is connected with a through-contacting (screw or cable) through the sample support up to its rear face.

The base of the sample holder is preferably also conductive or is conductive in particular local regions, so that an electrically conducting connection to the spiral spring can be produced. An electrically conductive connection leads from the base of the sample holder to the rear face of the sample support. This preferably takes place through an electrically conducting screw or a line.

In a particularly preferred embodiment for sample supports of non-conducting material, the helical spring passes through the beam entry opening in the base of the sample holder and rests on the conductor board lying therebehind, where it realizes at the same time the conducting connection to the rear face of the battery.

Contacts for the two poles of the battery of each individual sample holder (from the front face of the battery for example via cover, screw and cable, from the rear face of the battery for example via helical spring and base of the depression or directly via the helical spring) lie on the rear face of the sample support. In this manner of viewing, it is to be taken into account that the front face of the battery faces the front face of the sample support.

According to the invention, provision is now made to bring the contacts together on or at the centre axis of the sample support and from there to lead them in a defined manner to the current supply and/or to the measuring devices (e.g. potentiostats). This preferably takes place by a conductor board being arranged on the rear face of the sample support, which conductor board has conductor paths which lead from the contacts of each individual sample holder to the centre axis of the sample support. The conductor board is fixed here with respect to the sample support and thereby takes part in any rotary movements of the sample support during the positioning of a sample holder in the path of rays of an X-ray, synchrotron or other radiation source. In a particularly simple embodiment, the screw which produces the contacting of the battery front face, ends only in a corresponding contact in the conductor board. This can also be used advantageously for the fixing of the conductor board. Further preferably, the contacting of the rear face contact of the battery is realized by a screw, which also leads to the corresponding contact path of the conductor board and can also undertake the task of the mechanical mounting of the conductor board. It is known to the specialist in the art that mechanical spacers can be used as required, in order to realize a distance between the rear face of the sample support and the conductor board. The conductor board preferably consists of the usual material for such components, for example FR4 or polyimide.

In a preferred embodiment, the conductor board also has an opening for the passage of the beam.

Alternatively, individual lines or two-wire lines from the contacts of each sample holder to a busbar or respectively to a connector at the centre axis of the sample support are also possible.

In a preferred embodiment, the lines lead from each individual sample holder to a plug connection, for example a Molex connector, from where they are directed away as a bundle of individual lines or as a ribbon cable or round cable with a plurality of lines. The lines can then be supplied electrically and/or connected to measuring devices according to the measuring task.

Through the combined directing of all the cables of the different sample holders, it is possible in a much simpler manner to control the course of the cables and to keep it out of the path of rays. The distance of the movement of the combined cables from the centre axis is as small as possible and should preferably be no more than 50%, particularly preferably no more than 33% and most particularly preferably no more than 25% of the radius of the sample support distant from the centre axis.

In a further preferred embodiment, the sample supports are equipped with elements for the heating or cooling of the batteries (temperature-dependent measurements of battery materials). These are preferably Peltier elements here, which are arranged in the depressions. The current supply of these elements preferably takes place also via the shared plug connection or via a further connection, also arranged in the vicinity of the centre axis of the sample support. In a preferred embodiment, these elements for heating or cooling the batteries are configured in a similar manner to the adapter described above for batteries which have a smaller diameter than the depressions. They therefore lie as a ring around the batteries and control their temperature. A further embodiment provides the elements as a disc with a central hole, which are arranged between battery base and helical spring. Here, the elements are surrounded by a conductive casing, insulated electrically itself with respect to the elements, which casing ensures that an electrical connection is produced between the base of the battery and the helical spring. In a particularly simple embodiment, heating elements are provided, which are based on the principle of electric resistance heating.

The sample support according to the invention is preferably arranged on a holding device. This optionally offers adjustment possibilities, so that the sample holder of the sample which is being processed can be aligned as required. This is preferably possible in all three spatial directions. However, vertical or lateral adjustment are preferably possible also jointly or individually.

In a particularly preferred embodiment, it is possible to alter the alignment of the centre axis; particularly preferably from a horizontal alignment into a vertical (and intermediate values). Thus, the device according to the invention can be adapted not only to the beam direction but also can be changed from transmission diffractometry to reflection diffractometry.

The device according to the invention is suitable not only for measurements for powder diffraction in reflection- or transmission arrangement (incl. PDF measurements), but can also be used, preferably on synchrotron devices, for X-ray absorption measurements, neutron diffraction experiments, 3D tomography or Mössbauer/gamma-ray spectroscopy. With the presence of suitable heating or cooling arrangements, temperature-dependent measurements can also be carried out. A range within the usual limits of use between −60° C. and 100° C. is preferred here.

BRIEF DESCRIPTION OF THE DRAWINGS

The FIG. 3a and FIG. 3b show diagrammatically the cover 4 of the depression 51 of a sample holder in top view (3a) and in 3D view.

The FIG. 4a and FIG. 4b show diagrammatically the conductor board 7 in rear view (FIG. 4a) and in front view (FIG. 4b), wherein the front view illustrates the face facing the sample support 5 and represents the conductor paths.

DETAILED DESCRIPTION OF THE PREFERRED EMBODIMENTS

The following example embodiment explains the invention by way of example without, however, limiting it to the example configuration.

Figure 1:
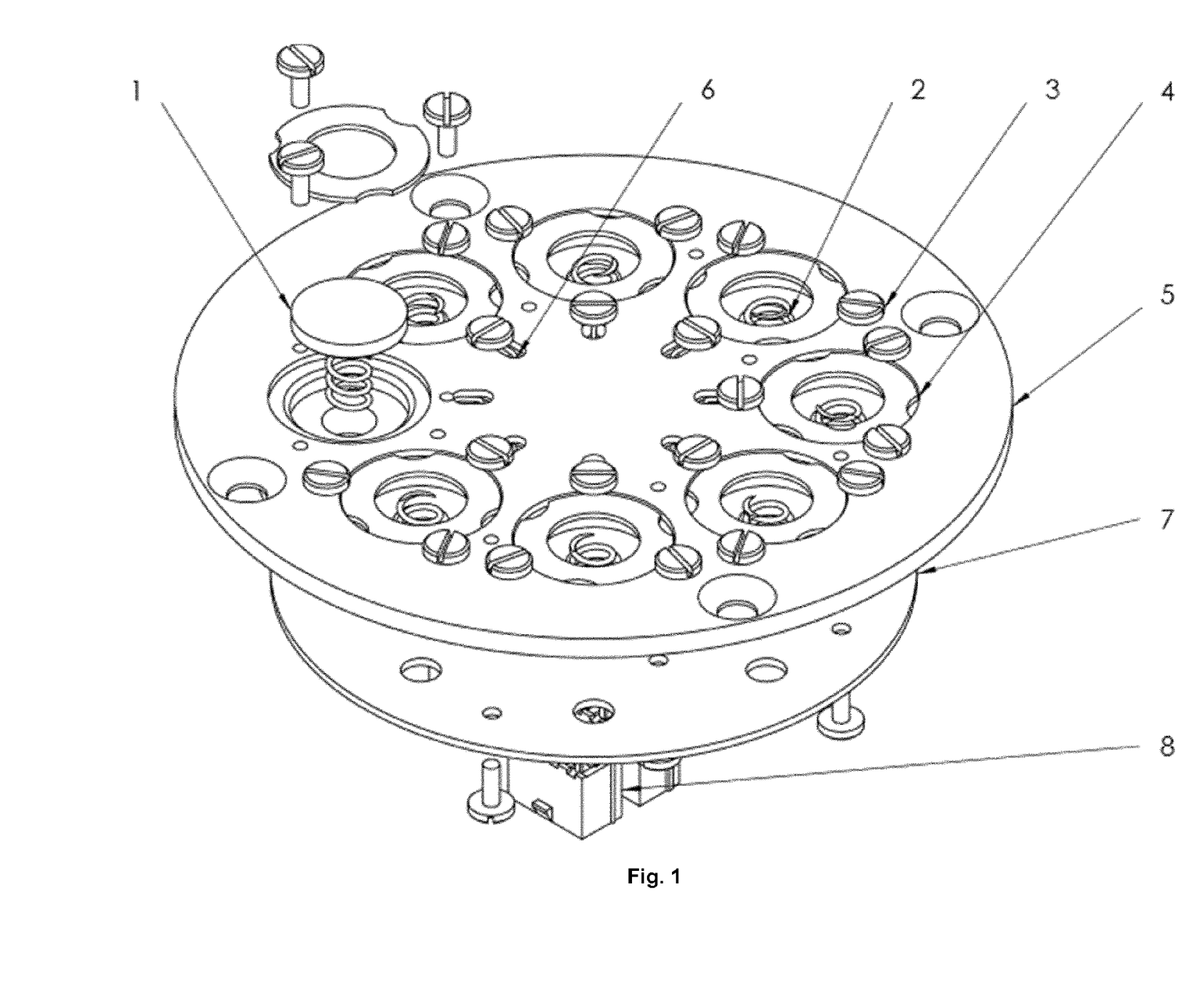
FIG. 1 shows diagrammatically the sample support 5 according to the invention, in 3D illustration.
Figure 2:
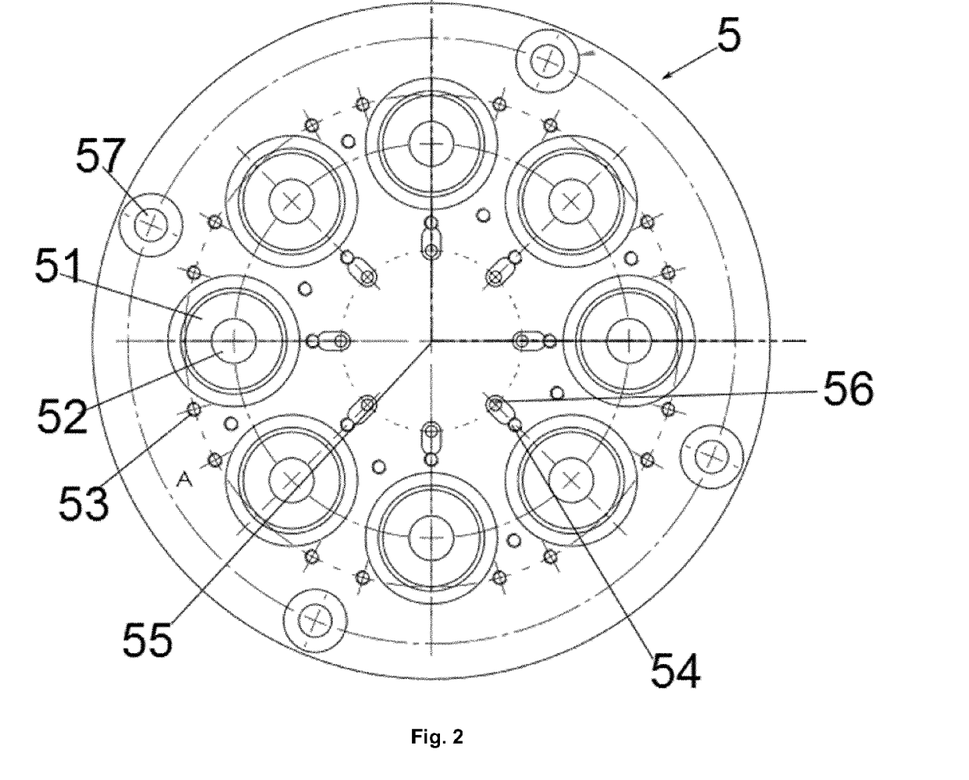
FIG. 2 illustrates the sample support 5 according to the invention in top view with the face (front face) facing away from the primary beam in the case of the transmission arrangement, therefore in diffraction direction (also designated "downstream region" in the case of synchrotron radiation). In particular, the centre axis 55 is thus illustrated, which extends perpendicularly through the plane of the drawing through the centre point of the circular sample support 5.
Figures 3A, 3B:
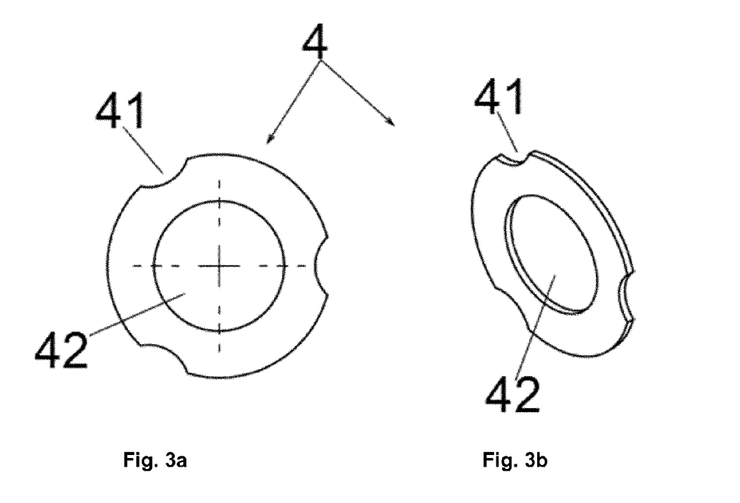
Figure 4A:
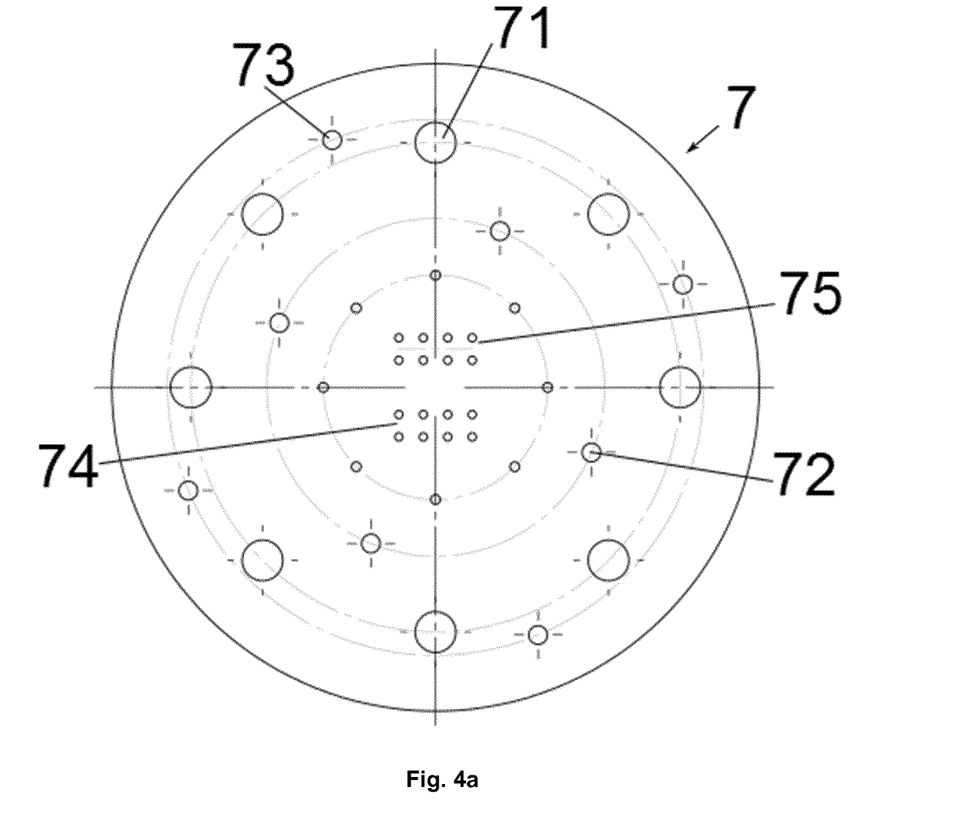
Figure 4B:
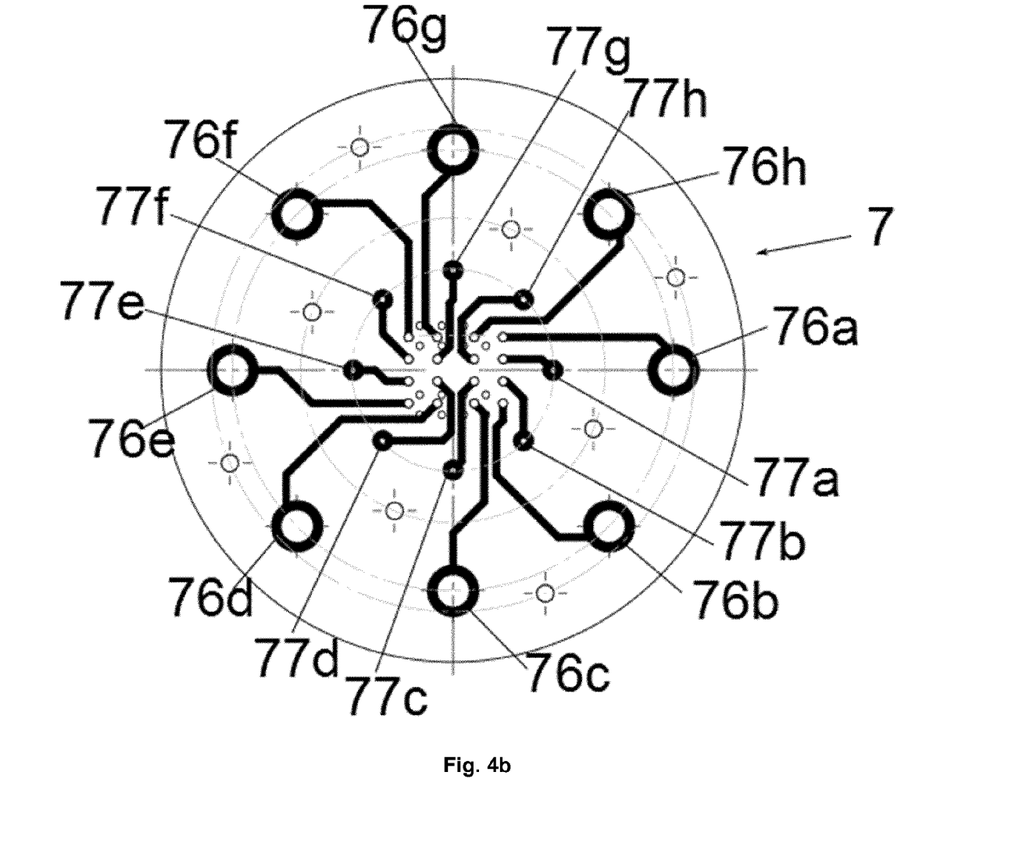

The sample support 5 consists of plastic and is embodied in a circular shape. The diameter of the sample support 5 is 144 mm. The sample support 5 is made from polyoxymethylene. The material thickness is 11 mm. Eight cylindrical depressions 51 with an internal diameter of 28 mm, which reduce after 1.4 mm to 20.6 mm, are arranged as sample holders around the centre axis 55 at a distance of 42 mm. Through the reduction of the internal diameters, shoulders are formed, on which the covers 4 can rest. The beam entry opening 52 in the base of the depression 51 has a diameter of 9.5 mm. Around each depression 51, three screw openings (53, 54) are arranged, wherein the screws lying nearest to the centre axis 55, which engage into the screw opening 54, are connected by means of a through-contacting (6) in an electrically conducting manner with the rear face and the conductor board 7 which is arranged there. The covers 4 consist of high-grade steel and have a beam entry opening 42 with a diameter of 16 mm. They can be arrested in the respective depression 51 by the recesses 41 being rotated so that they are congruent with the screw heads of the screws in the screw openings 53, 54, and the cover 4 can therefore be guided past them, into the depression 51. There, it presses the battery 1, which is raised by the helical spring 2, into the depression 51. After the twisting of the cover 4 through approximately 60°, the recesses 41 lie respectively between the screw heads of the screws in the screw openings 53, 54, and the cover 4 is interlocked behind the screw heads of the screws in the screw openings 53, 54. The battery 1 is pressed by the helical spring 2 against the cover and is guided laterally from the wall of the depression 51. Thus, the battery 1 is always situated in a defined, stable position in the sample support 5. The helical spring 2 emerges through the beam entry hole 52 in the base of the depression 51, rests on the conductor board 7 and contacts corresponding contact points 76a-76h there. These produce a conducting connection to one of the plug connectors 8 arranged at the centre axis 55. The conductor board 7 is rigidly connected to the sample support 5, so that it also follows the rotary movement of the sample support 5. From the front face of the sample support, the contact cables 6 arrive through the feedthrough 56 of the contact from the screw 54 to the rear face of the sample support 5. These contact cables 6 produce the electrically conducting connection between cover 4 and conductor board 7. For this, the cables 6 are connected to the associated contact points 77a-77h, from which likewise conductor paths lead to one of the plug connectors 8 arranged at the centre axis 55. A multi-core cable or a line bundle is advantageously connected via the plug connector 8. Owing to its flexibility, said multi-core cable or line bundle can tolerate rotary movements of the sample wheel, without being damaged or being pulled out from the plug connection. The specialist in the art is aware that this is only possible to a limited extent, however, and preferably a rotation in one rotation direction should be at least partially compensated in the next step by a rotation in the other direction (+/−180°).

"Advances in in situ powder diffraction of battery materials: a case study of the new beamline P02.1 at DESY, Hamburg", M. Herklotz et al. Journal of Applied Crystallography, (2013). 46. P. 1117-1127

Web page Anton Paar (http://www.anton-paar.com/?eID=documentsDownload&document=2065&L=8), status 18 Jun. 2014, "Multi-sample Chamber for In-situ Transmission XRD under Controlled Humidity" from online product brochure: "Sample Stages for Non-ambient X-ray Diffraction"

LIST OF REFERENCE NUMERALS 1 battery (button cell)
2 helical spring
3 screw for cover mounting
4 cover
41 recesses
42 beam entry opening
5 sample support
51 depression to receive battery
52 opening for beam exit in the base of the depression
53 opening for screw for fastening the cover
54 opening for screw for fastening the cover with contact
55 centre axis of the sample support (perpendicular to the plane of the drawing)
56 feedthrough of the contact from the screw to the rear face of the sample support
57 screw hole for fastening the sample support
6 cable as conductive connection to the rear face of the sample support
7 conductor board
71 beam exit opening in the conductor board
72, 73 openings for fastening screws of the conductor board
74, 75 solder openings for plug connector in the vicinity of the centre axis
76a-h contact points of the helical springs
77a-h contact points of the cables of the conductive connections from the front face (cover)
8 connector (for example Molex connector)

The invention claimed is:

1. A device for the in situ analysis of batteries (1) by means of X-ray, synchrotron or another radiation, having a sample support (5), which is embodied as a sample wheel rotatably mounted about the centre axis (55), which sample wheel has a plurality of sample holders, the centre points of which are arranged on a common circular line about the centre point of the sample support (5), wherein each sample holder can be repeatedly opened and closed individually by an arrestable cover (4), and the sample holder has in its interior a cavity which receives the battery (1), which is to be examined, in a manner ideal in shape with regard to circumference, wherein the cover (4) and the cavity have an unclosed or covered opening for the passage of the beam, and a spring (2), engaging in the edge region of the battery (1), presses the battery (1) against the cover (4), wherein the spring (2) and the edge region of the cover (4) are embodied so as to be electrically conducting but insulated with respect to one another, characterized in that there are directed from each sample holder an electrically conductive connection (6) from the edge region of the cover (4), and an electrically conductive connection by means of the spring (2) onto the face of the sample support (5) facing away from the cover (4) and from there into the vicinity of the centre point of the sample support (5), and the lines of all sample holders are combined there to form a line bundle or a plug connector (8).

2. The device according to claim 1, characterized in that the electrically conductive connections from the battery (1) via the spring (1) and from the battery (2) via the cover (4) on the face of the sample support (5) facing away from the cover (4) are contacted via contact points (76, 77) on a conductor board (7) and are brought together in the vicinity of the centre axis (55).

3. The device according to claim 2, characterized in that the spring (2) is a spiral spring and emerges through the beam exit hole in the base of the sample holder (5) and rests on the conductor board (7) and is suitable to produce an electrically conductive connection between the rear face of the battery (1) in the sample holder and a contact point (76) on the conductor board (7).

4. The device according to claim 1, characterized in that the sample wheel is arranged so as to be rotatable manually or by means of a drive such that a sample holder can be introduced into the path of rays of an X-ray, synchrotron or other radiation source.

5. The device according to claim 4, characterized in that the device is arranged in a supporting device, through which the position of the sample wheel can be altered so that the position of the sample holder in the path of rays can be altered in one or more of the three spatial directions and/or the inclination of the centre axis to the axis of the path of rays can be altered.

* * * * *